United States Patent [19]

McGlave et al.

[11] Patent Number: 5,523,286

[45] Date of Patent: Jun. 4, 1996

[54] STROMA-DERIVED PROTEOGLYCAN CONTAINING COMPOSITION WHICH PROMOTES DIFFERENTIATION AND MAINTAINS THE SELF-RENEWAL CAPACITY OF LONG-TERM BONE MARROW CULTURE-INITIATING CELLS

[75] Inventors: Philip B. McGlave; Catherine M. Verfaillie, both of St. Paul, Minn.

[73] Assignee: Regents of the University of Minnesota, Minneapolis, Minn.

[21] Appl. No.: 152,051

[22] Filed: Nov. 12, 1993

[51] Int. Cl.$^6$ .................. A61K 38/16; A61K 38/00; C08B 37/10; C08B 37/08; C12N 5/00

[52] U.S. Cl. .................. 514/8; 514/21; 536/21; 536/20; 435/240.2; 435/240.21; 435/240.3

[58] Field of Search .................. 435/240.1, 240.2, 435/240.21, 240.3, 240.31, 70.1; 514/8, 21; 424/93.7; 536/21, 20

[56] References Cited

PUBLICATIONS

J. Brandt et al., *Blood*, 79, 634 (1992) is cited in the specification at p. 6, line 20.
J. Brandt et al., *J. Clin. Invest.*, 82, 1017 (1988) is cited in the specification at p. 6, line 8.
J. Brandt et al., *J. Clin. Invest.*, 86, 932 (1990) is cited in the specification at p. 5, line 21 and at p. 6, line 25.
J. Caldwell et al., *J. Cell Physiol.*, 147, 344 (1991) is cited in the specification at p. 6, line 36.
T. M. Dexter et al., *J. Cell Physiol.*, 91, 335 (1977) is cited in the specification at p. 3, line 30.
C. J. Eaves et al., *Blood*, 78, 110 (1991) is cited in the specification at p. 5, line 16.
F. A. Fletcher et al., *Blood*, 76, 1098 (1990) is cited in the specification at p. 6, line 16.
S. Gartner et al., *PNAS USA*, 77, 4756 (1980) is cited in the specification at p. 4, line 8.
M. Y. Gordon et al., *J. Cell. Physiol.*, 130, 150 (1987) is cited in the specification at p. 4, line 16.
D. N. Haylock et al., *Blood*, 80, 1405 (1992) is cited in the specification at p. 5, line 24.
S. Huang et al., *Nature*, 360, 745 (1992) is cited at the specification at p. 6, line 23.

K. Ikebuchi et al., *PNAS USA*, 85, 3445 (1988) is cited at the specification at p. 6, line 6.
E. L. W. Kittler et al., *Blood*, 79, 3168 (1992) is cited in the specification at p. 5, line 15 and at p. 6, line 37.
A. G. Leary et al., *Blood*, 71, 1759 (1988) is cited in the specification at p. 6, line 9.
G. Migliascio et al., *Blood*, 79, 2620 (1992) is cited in the specification at p. 5, line 23.
S. R. Paul et al., *PNAS USA*, 87, 7512 (1990) is cited in the specification at p. 4, line 12.
F. T. Slovick et al., *Exp. Hematol.*, 12, 327 (1984) is cited in the specification at p. 4, line 9.
L. W. M. M. Terstappenet et al., *Blood*, 77, 1218 (1991) is cited in the specification at p. 5, line 22.
K. Tsuji et al., *Blood*, 79, 2855 (1992) is cited in the specification at p. 6, line 13.
C. M. Verfaillie, *Blood*, 79, 2821 (1992) is cited in the specification at p. 4.
C. M. Verfaillie et al., *J. Exp. Med.*, 172, 509 (1990) is cited in the specification at p. 2, line 33; at p. 8, line 1; at p. 13, line 28 at p. 16, line 24; at p. 17, line 5; and at p. 18, lines 4, 7, 15 and 17.
K. M. Zsebo et al., *Cell*, 63, 195 (1990) is cited in the specification at p. 6, line 21.
Suzu et al, *J. Biol. Chem.*, 267(24), pp. 16812–16815 (Aug. 25, 1992).
Suzu et al., *J. Biol. Chem.* 267(7), pp. 4345–4348 (Mar. 5, 1992).
Oppenheim et al, "Immunophysiology—The Role of Cells & Cytokines in Immunity & Inflammation" published by 1990 by Oxford Press (NY), pp. 166–193.

*Primary Examiner*—Marian C. Knode
*Assistant Examiner*—Susan M. Dadio
*Attorney, Agent, or Firm*—Schwegman, Lundberg & Woessner

[57] ABSTRACT

An anionic macromolecular containing composition is disclosed that is capable of supporting conservation and differentiation of long-term bone marrow culture initiating cells in cultured mammalian hematopoietic cells. The composition disclosed is a mixture of glycoproteins, more specifically proteoglycans, which are of a molecular weight greater than 200 kD.

4 Claims, 6 Drawing Sheets

STROMA-DERIVED PROTEOGLYCAN CONTAINING COMPOSITION WHICH PROMOTES DIFFERENTIATION AND MAINTAINS THE SELF-RENEWAL CAPACITY OF LONG-TERM BONE MARROW CULTURE-INITIATING CELLS

This invention was made with the support of NIH grant number R01-CA-45814-01. The Government has certain rights in the invention.

BACKGROUND OF THE INVENTION

The human hematopoietic system is populated by cells of several different lineages. These "blood cells" may appear in bone marrow, the thymus, lymphatic tissue(s) and in peripheral blood. Within any specific lineage, there are a number of maturational stages. In most instances, the more immature developmental stages occur within bone marrow while the more mature and final stages of development occur in peripheral blood.

There are two major lineages: The myeloid lineage which matures into red blood cells, granulocytes, monocytes and megakaryocytes; and the lymphoid lineage which matures into B lymphocytes and T lymphocytes. Within each lineage and between each lineage, antigens are expressed differentially on the surface and in the cytoplasm of the cells in a given lineage. The expression of one or more antigens and/or the intensity of expression can be used to distinguish between maturational stages within a lineage and between lineages.

Assignment of cell to lineage and to a maturational stage within a cell lineage indicates lineage commitment. There are cells, however, which are uncommitted to any lineage (i.e., "progenitor" cells) and which, therefore, retain the ability to differentiate into each lineage. These undifferentiated, pluripotent progenitor cells will hereinafter be referred to as the "stem cells."

All of mammalian hematopoietic cells can, in theory, be derived from a single stem cell. In vivo, the stem cell is able to self-renew, so as to maintain a continuous source of pluripotent cells. In addition, when subject to particular environments and/or factors, the stem cells may differentiate to yield dedicated progenitor cells, which in turn may serve as the ancestor cells to a limited number of blood cell types. These ancestor cells will go through a number of stages before ultimately yielding mature cells.

The benefit of obtaining a pure population of stem cells is most readily recognized in the field of gene therapy. Gene therapy seeks to replace or repopulate the cells of the hematopoietic system which contain a defective gene with cells that do not contain the defective gene but instead contain a "normal" gene. Using conventional recombinant DNA techniques, a "normal" gene is isolated, placed into a viral vector, and the viral vector is transfected into a cell capable of expressing the product coded for by the gene. The cell then must be introduced into the patient. If the "normal" gene product is produced, the patient is "cured" of the condition. The difficulty is that the transformed cells must be capable of continual regeneration as well as growth and differentiation.

Although stem cells are potentially optimal "hosts" for transformation, substantial problems have been encountered in (a) identifying the antigenic markers unique to stem cells, (b) isolating homogenous populations comprising substantial numbers of non-lineage committed, pluripotent stem cells and (c) maintaining and, possibly, expanding populations of human stem cells.

However, a number of research groups have recently reported the isolation of populations of mammalian bone marrow cell populations which are enriched to a greater or lesser extent in pluripotent stem cells. For example, C. Verfaillie et al., *J. Exp. Med.*, 172, 509 (1990) reported that a two-step purification of low density human bone marrow cells by negative immunomagnetic selection and positive dual-color fluorescence activated cell sorting (FACS) yielded a $Lin^-/CD34^+/HLA-DR^-$ cell fraction that was 420-fold enriched in pluripotent stem cells capable of initiating long-term bone marrow cultures (LTBMC) over unmanipulated bone marrow mononucleocytes (BMMNC) obtained after Ficoll-Hypaque separation. This group reported that the combination of positive selection for small blast-like cells that are CD34 antigen positive but HLA-DR antigen negative, combined with a more extensive negative selection to deplete the population of CD2, CD19 and CD71, results in an about two- to three-fold greater enrichment in pluripotent stem cells over that previously reported.

The development of cell culture media and conditions that will maintain stem cells in vitro for the extended periods of time required for the procedures involved in gene therapy, identification of growth factors, thorough characterization of cell morphologies and the like, has presented a unique set of obstacles. To date, successful in vitro stem cell cultures have depended on the ability of the laboratory worker to mimic the conditions which are believed to be responsible for maintaining stem cells in vivo.

For example, hematopoiesis occurs within highly dense cellular niches within the bone marrow in the adult and in similar niches within the fetal yolk sac and liver. Within these niches, stem cell differentiation is regulated, in part, through interactions with local mesenchymal cells or stromal cells. Mammalian hematopoiesis has been studied in vitro through the use of various long-term marrow culture systems. T. M. Dexter et al., in *J. Cell Physiol.*, 91, 335 (1977) described a murine system from which spleen colony-forming units (CFU-S) and granulocyte/macrophage colony forming units (CFU-GM) could be detected for several months, with erythroid and megakaryocytic precursors appearing for a more limited time. Maintenance of these cultures was dependent on the formation of an adherent stromal cell layer composed of endothelial cells, adipocytes, reticular cells, and macrophages. These methods were soon adapted for the study of human bone marrow. Human long-term culture systems were reported to generate assayable hematopoietic progenitor cells for 8 or 9 weeks, and, later, for up to 20 weeks (See, S. Gartner et al., *PNAS USA*, 77, 4756 (1980); F. T. Slovick et al., *Exp. Hematol.*, 12, 327 (1984). Such cultures were also reliant on the preestablishment of a stromal cell layer which must frequently be reinoculated with large, heterogeneous populations of marrow cells. Hematopoietic stem cells have been shown to home and adhere to this adherent cell multilayer before generating and releasing more committed progenitor cells (M. Y. Gordon et al., *J. Cell. Physiol.*, 130, 150 (1987)).

Stromal cells are believed to provide not only a physical matrix on which stem cells reside, but also to produce membrane-contact signals and/or hematopoietic growth factors necessary for stem cell proliferation and differentiation. This heterogeneous mixture of cells comprising the adherent cell layer presents an inherently complex system from which the isolation of discrete variables affecting stem cell growth has proven difficult. Furthermore, growth of stem cells on a stromal layer makes it difficult to recover the hematopoietic cells or their progeny efficiently.

C. M. Verfaillie, in *Blood*, 79, 2821 (1992) and P. McGlave et al., in U.S. patent application Ser. No. 07/862,814, filed Apr. 3, 1992, now U.S. Pat. No. 5,436,151, demonstrated that primitive, lineage-non-committed $CD34^+/HLA-DR^-$ cells can differentiate and can be maintained when cocultured with stromal layers but separated from the stromal layers by a 0.4 µm microporous membrane ("stroma non-contact" culture). In U.S. patent application Ser. No. 08/032,670, filed Mar. 17, 1993, P. McGlave and C. Verfaillie demonstrated that $Lin^-/CD34^+/DR^-$ cells can differentiate and proliferate when they are cultured without a stromal layer ("stroma free culture") but are supplemented daily by media conditioned by normal allogeneic bone marrow stromal layers. These studies suggest that soluble factors derived from the bone marrow stromal layer are capable of inducing differentiation of primitive human hematopoietic cells and can conserve at least a fraction of more primitive progenitors.

One role of the stromal cells in stroma-dependent cultures may be to provide a combination of cytokines that promote differentiation and proliferation of primitive hematopoietic progenitors. See, for example, E. L. W. Kittler et al., *Blood*, 79, 3168 (1992) and C. J. Eaves et al., *Blood*, 78, 110 (1991). Long-term cultures can indeed be established from primitive hematopoietic progenitors in the absence of an adherent stromal layer when defined cytokines are repeatedly added. See, for example, J. Brandt et al., *J. Clin. Invest.*, 86, 932 (1990); L. W. M. M. Terstappenet ed., *Blood*, 77, 1218 (1991); G. Migliascio et al., *Blood*, 79, 2620 (1992) and D. N. Haylock et al., *Blood*, 80, 1405 (1992). Cytokines thought to be important in the induction of differentiation and/or proliferation of primitive hematopoietic progenitors are listed on Table 1, below.

TABLE 1

| Cytokine | Reference |
| --- | --- |
| rhuG-CSF* | K. Ikebuchi et al., PNAS USA, 85, 3445 (1988) |
| rhuIL-1, rhuIL-6, rhuIL-3 | J. Brandt et al., J. Clin. Invest., 82, 1017 (1988); A. G. Leary et al., Blood, 71, 1759 (1988) |
| rhuIL-11 | S. R. Paul et al., PNAS USA, 87, 7512 (1990); K. Tsuji et al., PNAS USA, 87, 7512 (1990) |
| LIF (leukemia inhibitory factor) | F. A. Fletcher et al., Blood, 76, 1098 (1990) |
| SCF (ligand for c-Kit) | J. Brandt et al., Blood, 79, 634 (1992); K. M. Zsebo et al., Cell, 63, 195 (1990) |
| bFGF | S. Huang et al., Nature, 360, 745 (1992) |
| rhuGM-CSF | J. Brandt et al., J. Clin. Invest., 86, 932 (1990) |

*rhu = recombinant human

Although mRNA transcripts for almost all these cytokines are constitutively expressed or can be induced in stromal cells, detection of cytokines in stroma conditioned media with either immunological methods or bioassays has been limited to IL-6, G-CSF, GM-CSF and SCF. See, J. Caldwell et al., *J. Cell Physiol.*, 147, 344 (1991); E. L. W. Kittler et al., *Blood*, 79, 3168 (1992).

The role of cytokines in the hematopoiesis occurring in long-term bone marrow cultures remains uncertain, and the factors that regulate both self-replication and the initial differentiation process of primitive uncommitted hematopoietic progenitors are still largely unknown. Therefore, there is a continuing need to characterize and evaluate factors produced by the stromal cells in long-term cultures, and to uncover and elucidate the mechanisms underlying the self-replication and initial differentiation of the human hematopoietic stem cell. Characterization of such stroma-derived factor(s) may have important clinical applications, such as in vitro stem cell expansion for use in cancer treatment and gene therapy.

SUMMARY OF THE INVENTION

Culturing very primitive human hematopoietic progenitors in "stroma-free" cell culture media which is supplemented with Il-3, LIF, G-CSF and SCF, four early acting cytokines, yields cell expansion that is similar to that achieved in "stroma-non-contact" cultures supplemented with the same cytokines. However, we discovered that generation of committed progenitors and conservation of the more primitive long term bone marrow culture-initiating cells (LTBMC-IC) is far superior in "stroma-non-contact" cultures supplemented with or without IL3 than in "stroma-free" cultures supplemented with IL3 alone or a combination of IL3, LIF, G-CSF and SCF. These studies indicate that human bone marrow stromal layers produce soluble factors that can, either alone or in synergy with certain preselected cytokines, (1) conserve primitive long-term bone marrow culture-initiating cells (LTBMC-IC), (2) induce early differentiation of a fraction of the primitive progenitors (the "stem cells") and (3) prevent their terminal differentiation. These stroma-derived factors are not the known early-acting cytokines IL3, SCF, LIF or G-CSF.

Therefore, the present invention provides a stroma-derived anionic fraction comprising at least one macromolecule which, in combination with cytokines, can support conservation and differentiation of long-term bone marrow culture-initiating cells (LTBMC-IC), preferably in stem-cell enriched cultured hematopoietic cells, such as the $Lin^-/CD34^+/HLA-DR^-$ cells disclosed by C. Verfaillie et al., *J. Exp. Med.*, 172, 509 (1990). The anionic macromolecule-containing composition is prepared by a process comprising subjecting stroma cell conditioned aqueous culture medium to ion-exchange chromatography so as to isolate an anionic glycoprotein fraction having a molecular weight of greater than 200 kD as measured by SDS-PAGE under reducing conditions that can support conservation and differentiation of LTBMC-IC in cultured hematopoietic cells to essentially the same extent as does culture media conditioned by stromal cells, taught in U.S. patent application Ser. No. 08/032,670, cited above.

It is believed that the bioactive anionic macromolecular fraction comprises a mixture of glycoproteins, including proteoglycans. Glycoproteins are polysaccharide/protein complexes which can have a variable carbohydrate content. Larger carbohydrate groups are present in glycoproteins having a structural function, while glycoproteins and those that contain oligosaccharides are generally related to molecular or cell recognition. For example, proteoglycans (also called mucopolysaccharides) are glycoproteins which consist of approximately 95% or greater polysaccharides and approximately 5% protein and are present in many fluids and tissues. The polysaccharide chains in proteoglycans are termed glucosaminoglycans (GAG's).

More specifically, the anionic macromolecular fraction is believed to comprise a mixture of proteoglycans which contain heparan sulfate and chondroitin sulfate as their glycosaminoglycans. These macromolecule(s) are believed to be substantially responsible in the maintenance of LTBMC-IC observed in "stroma non-contact" cultures of hematopoietic cells, and to the superiority of stroma non-contact cultures over "stroma-free" cultures with added cytokines. Furthermore, a combination of the present anionic macromolecular fraction with exogenous cytokines supported conservation and differentiation of LTBMC-IC to at least the same extent as stroma conditioned medium, prepared as taught in U.S. patent application Ser. No. 08/032,670, cited above, while either component alone failed to do so.

Thus, the present invention also provides a method for the long-term culture of mammalian, preferably murine or human, hematopoietic cells. As used herein, the term "hematopoietic cells" includes both the uncommitted, pluripotent "stem cells" described above, as well as the lineage-committed, or dedicated, progenitor cells which can develop into mature "blood cells" and mixtures thereof. Thus, the present method is effective to maintain the stem cell population in a population of hematopoietic cells such as the Lin$^-$/CD34$^+$/HLA-DR$^-$ marrow cell population and the less selected CD34$^+$ enriched population described above. The ability of the present method to maintain and/or expand the population of stem cells within a cell population can be evaluated by determining the continuing presence/number of cells capable of initiating long-term bone marrow cultures (LTBMC-IC) as disclosed hereinbelow. The presence of these cells after at least 5–8 weeks of culturing a given population of cells provides art-recognized confirmation that stem cells have been preserved and/or expanded.

The present factor is also effective to derive and expand committed progenitors both from such stem cell populations, as well as from already committed progenitor cells, such as those from sources such as human bone marrow, human newborn cord blood, fetal liver and adult human peripheral blood. The existence and number of committed progenitors can be determined by assaying for colony-forming cells (CFC) as disclosed hereinbelow. Preferably, the populations are both human and allogeneic, most preferably they are autologous, although they need not be.

Thus, the present method at least substantially conserves the stem cell population throughout the culturing period, while preserving, and preferably enhancing, its ability to differentiate into lineage-committed progenitor cells (hereinafter referred to as "committed progenitors"). The present method can also be used to derive and expand committed progenitors (CFC) from already committed progenitor cell populations. As used herein, the term "stromal cells" includes (1) human allogeneic or autologous stromal cells, or non-human stromal cells, (2) human or non-human stromal cell lines which need not be hematopoietic, and (3) human or non-human virally infected cell lines, such as immortalized embryonic fibroblasts which are effective to provide "feeder layers" for stem cell populations.

The present method also greatly facilitates the characterization and isolation of cultured human stem cells, or of more various hematopoietic cell populations containing said stem cells but not containing a stromal cell "feeder layer," since the method does not employ direct or indirect contact between the stromal cell layer and the hematopoietic cells.

Unless stated otherwise, molecular weights given below were determined by SDS-PAGE under reducing conditions.

DETAILED DESCRIPTION OF THE INVENTION

Figure 1:
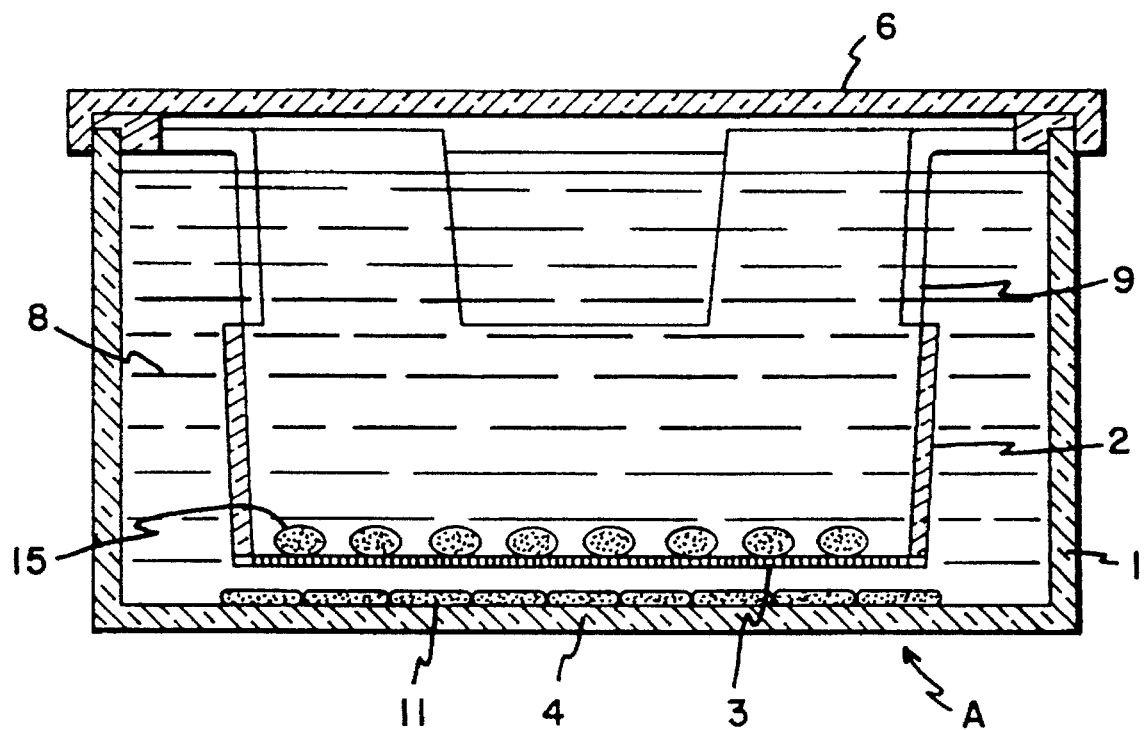
FIG. 1 is a schematic cross-sectional view of a cell culture chamber useful in the present method.

A. Isolation of Hematopoietic Cells Enriched with Stem Cells

The stem cell population constitutes only a small percentage of the total number of leukocytes in bone marrow. Additionally, at the present time, antigens present on stem cells alone or which are also present on more differentiated progenitors have not been fully identified. As in mice, one marker which has been indicated as present on human stem cells, CD34, is also found on a significant number of lineage committed progenitors. Another antigen which provides for some enrichment of progenitor activity is Class II HLA (particularly a conserved DR epitope recognized by a monoclonal antibody designated J1-43). However, these markers are also found on numerous lineage committed hematopoietic cells. The Thy-1 molecule is a highly conserved protein present in the brain and in the hematopoietic system of rat, mouse and man. These species differentially express this antigen and the true function of this molecule is unknown. However, the Thy-1 molecule has been identified on rat and mouse hematopoietic stem cells. This protein is also believed to be present on most human bone marrow cells, but may be absent on stem cells.

Isolation of populations mammalian bone marrow cell populations which are enriched to a greater or lesser extent with pluripotent stem cells can be achieved through the use of these and other markers. For example, monoclonal antibody My-10, which is found on progenitor cells within the hematopoietic system of non-leukemic individuals, is expressed on a population of progenitor stem cells recognized by My-10 (i.e., express the CD34 antigen) and can be used to isolate stem cells for bone marrow transplantation. See Civin, U.S. Pat. No. 4,714,680. My-10 has been deposited with the American Type Culture Collection (Rockville, Md.) as HB-8483 and is commercially available from Becton Dickinson Immunocytometry Systems ("BDIS") as anti-HPCA 1. However, since using an anti-CD34 monoclonal antibody alone is not sufficient to distinguish between "stem cells," and the true pluripotent stem cell (B cells (CD19$^+$)

and myeloid cells (CD33$^+$) make up 80–90% of the CD34$^+$ population), a combination of monoclonal antibodies must be used to select human progenitor stem cells.

For example, a combination of anti-CD34 and anti-CD38 monoclonal antibodies can be used to select those human progenitor stem cells that are CD34$^+$ and CD38$^-$. One method for the preparation of such a population of progenitor stem cells is to stain the cells with immunofluorescently labelled monoclonal antibodies. The cells then may be sorted by conventional flow cytometry with selection for those cells that are CD34$^+$ and those cells that are CD38$^-$. Upon sorting, a substantially pure population of stem cells results. (Becton Dickinson Company, published European Patent Application No. 455,482)

Additionally, negative selection of differentiated and "dedicated" cells from human bone marrow can be utilized to yield a population of human hematopoietic stem cells with fewer than 5% lineage committed cells. See Tsukamoto et al., U.S. Pat. No. 5,061,620. The stem cells that result are characterized as being CD34$^+$, CD3$^-$, CD7$^-$, CD8$^-$, CD10$^-$, CD14$^-$, CD15$^-$, CD19$^-$, CD20$^-$, CD33$^-$, Class II HLA$^+$ and Thy-1$^+$.

Furthermore, a two-step purification of low density human bone marrow cells by negative immunomagnetic selection and positive dual-color fluorescence activated cell sorting (FACS) can be used to yield a Lin$^-$/CD34$^+$/HLA-DR$^-$ cell fraction that is 420-fold enriched in pluripotent stem cells capable of initiating long-term bone marrow cultures (LTBMC) over unmanipulated bone marrow mononucleocytes (BMMNC) obtained after Ficoll-Hypaque separation. See C. Verfaillie et al., *J. Exp. Med.*, 172, 509 (1990) (Hereinafter C. Verfaillie et al.). The combination of positive selection for small blast-like cells that are CD34 antigen positive but HLA-DR antigen negative, combined with a more extensive negative selection to deplete the population of CD2, CD19 and CD71, results in an about two- to three-fold greater enrichment in pluripotent stem cells over that previously reported.

B. Isolation of Stroma-Derived Anionic Fraction

The anionic molecules present in stroma conditioned media can be isolated utilizing ion-exchange chromatography. Stromal conditioned media can be prepared by growing stromal cells to confluency in media and then killing the non-stromal cells via irradiation. The media suspended cells are then removed and the stroma cells are cultured in fresh media. About 48 hours after replacing half of the media with fresh media, the supernatant can be collected and either analyzed immediately or frozen at −70° C. until analyzed. The anionic fraction can then be isolated from the supernatant by high performance liquid chromatography (HPLC).

Preferably, the ion-exchange chromatography is accomplished by high pressure liquid chromatography on a suitable anion-exchange support such as DEAE-Sephacel resin (diethylaminoethyl-modified cellulose), PEI Cellulose, QAE Cellulose and the like. Other suitable anion exchange chromatographic supports are disclosed in Sigma Chem. Co., Biochemicals/Organic Compounds for Research, and Diagnostic Reagents (1993) at pages 1585–1594.

C. Culture of Hematopoietic Cells in a "Stroma Non-Contact" System

In the "stroma non-contact" system, the hematopoietic cell population is physically supported by a culture substratum such as a microporous hollow fiber on a microporous membrane which maintains the hematopoietic cells and any associated cells in contact with a liquid culture medium. The pores of the membrane or the hollow fibers can vary in size, so long as they allow culture medium and its components to contact the hematopoietic cells, while providing adequate support for the cells. Preferably, the microporous membrane or the hollow fibers are formed of a synthetic polymer, which can be coated with a cell-adherence promoting peptide, such as mammalian (human) collagen, laminin, fibronectin or the subunits thereof possessing the ability to promote hematopoietic cell attachment. For example, such peptides are disclosed in U.S. Pat. Nos. 5,019,546, and 5,059,425.

The hematopoietic cells may be attached to the interior of a microporous tube or hollow fiber, while the stromal cells are maintained in a fixed relationship from the exterior of the tubing, e.g., on the walls of a chamber containing the growth medium.

During the practice of the present method, the liquid growth medium may be held as a stationary body which envelops both populations of cells, and is preferably about 25–100% exchanged at fixed intervals, e.g., of 8 hrs—14 days, preferably of about 1–10 days. Alternatively, the culture medium can be continuously circulated through a culture chamber that contains the hematopoietic cells and replaced/replenished at a site remote from the culture chamber.

One commercially-available device suitable for use with the present method is the Transwell™ series of cell culture chambers available from Costar Corp., Cambridge, Mass., USA. As depicted in schematic cross-section in FIG. 1, each Transwell® chamber (A) comprises a flat-bottomed plastic lower compartment 1, and a plastic upper compartment 2, which can be removably inserted into compartment 1, so that the collagen-coated, microporous membrane 3 (0.45 μm pore diameter), which forms the bottom of compartment 2, is held in a fixed, essentially parallel relationship to the inner surface of the bottom (4) of the compartment. This assembly is covered by a removable lid 6. In use, a preselected amount of liquid culture medium 8 is added to the lower compartment 1. Stem cells or other hematopoietic cells 15 are added to the upper surface of microporous membrane 3 and the upper compartment (or transwell) 2 is inserted into the lower compartment. Opening 9 in the sidewall of the transwell 2 permits addition of or removal of the medium 8 from the exterior void space of the chamber A. The cover 6 is then replaced. Following the culture period, which can be as long as 3–6 months, the cover 6 is removed; the transwell is removed, and all or a portion of the cells 15 are then removed from the microporous membrane and employed in the end use.

The invention will be further described by reference to the following detailed examples, wherein human bone marrow was obtained from 22 healthy young volunteers after informed consent by aspiration from the posterior iliac crest in preservative free heparin. Bone marrow mononuclear cells (BMMNC) were obtained after Ficoll-Hypaque separation (Sigma Diagnostics, St. Louis, Mo.) (s.g. 1.077).

Cultured hematopoietic cells were assayed in the short term methylcellulose assay for the presence of committed progenitors. In the short-term methylcellulose assay, the Lin$^-$/CD34$^+$/HLA-DR$^-$ cells were plated in clonogenic methylcellulose assay supplemented with 3 IU recombinant erythropoietin (Epoetin) (Amgen, Thousand Oaks, Calif.) and 10% conditioned media from the bladder carcinoma cell line 5637 as described by C. Verfaillie et al. Cultures were incubated in a humidified atmosphere at 37° C. and 5% $CO_2$ for 18-21 days. The cultures were assessed at day 18-21 of culture for the presence of CFU-MIX, granulocyte/macrophage colony forming units (CFU-GM) and erythroid burst-forming units (BFU-E) as described by C. Verfaillie et al.

To carry out limiting dilution assays (LDA) for LTBMC-IC, at day zero $Lin^-/CD34^+/HLA-DR^-$ cells (24 replicates per concentration) were plated onto $3 \times 10^4$ irradiated allogenic stromal cells, subcultured in 96 well plates (Costar). See H. J. Sutherland et al., *Blood*, 78, 666 (1991) and *PNAS USA*, 87, 2584 (1990). Cultures were maintained in a humidified atmosphere, at 37° C. and 5% $CO_2$ and treated weekly with 75 µl fresh media. At week 5, nonadherent and adherent cells were collected as described in C. Verfaillie at al. and evaluated for the presence of committed progenitors. The absolute number of LTBMC-IC present in the different cell populations was calculated as the reciprocal of the concentration of test cells that gave 37% negative cultures using the Poisson statistics (E. H. Proter et al., *J. Cancer*, 17, 583 (1963)) and the weighted mean method (C. Taswell, *J. Immunol.*, 126, 1614 (1981)).

Results of experimental points obtained from multiple experiments were reported as the mean ±1 standard error of the mean (SEM). Significance levels were determined by two-sided students t-test analysis.

EXAMPLE 1

Bone marrow mononuclear cells (BMMNC) were purified further in an initial counterflow elutriation step, by suspending BMMNC in phosphate buffered saline (PBS) supplemented with 0.3% bovine serum albumin (BSA) (Sigma) and 0.01% ethylene diamine tetraacetic acid (EDTA) (Sigma). The cells were injected into an elutriator system with standard separation chamber (Beckman Instruments, Inc., Palo Alto, Calif.) primed with Iscove's Modified Dulbecco's Medium (IMDM), 5% fetal calf serum (FCS) and 0.01% EDTA. Rotor speed and temperature were maintained at 1,950 RPM and 10° C. After loading, 200 ml of effluent was collected at a flow rate of 14 ml/min. The rotor was then stopped and the remaining BMMNC flushed from the separation chamber. Cells collected in fraction 14 were then depleted from T-lymphocytes and NK cells by sheep erythrocyte rosetting as described by C. M. Verfaillie et al., *Blood*, 77, 263 (1991). Further depletion of committed lymphoid and myeloid/monocytic cells was obtained by negative immunomagnetic depletion of cells expressing CD2, CD3, CD11b, CD19, CD56, CD71, MY8 and glycophorin-A antigens using the methods described in C. Verfaillie et al.

The resultant lineage negative ($Lin^-$) cells were labeled with anti-CD34 and anti-HLA-DR antibodies as described by C. Verfaillie et al. Cells were sorted on a FACS-Star-Plus laser flow cytometry system (Becton-Dickinson, Mountain View, Calif.) equipped with a Consort 40 computer. Cells were initially selected for low vertical and very low/low horizontal light scatter properties. Cells selected in the first window expressing high numbers of CD34 antigens and lacking HLA-DR antigen expression were then sorted to yield $Lin^-/CD34^+/HLA-DR^-$ cells, as described by C. Verfaillie, et al. These $Lin^-/CD34^+/HLA-DR^-$ cells correspond to the highly stem cell-enriched population designated as $Lin^-34^+DR^-$ in C. Verfaillie et al. The latter windows were chosen on the basis of the fluorescence pattern of control samples labeled with mouse IgG1-PE and mouse IgG2a-FITC antibodies.

EXAMPLE 2

Isolation of Stroma-Derived Anion Fraction

1. Preparation of Stroma Conditioned Media

Murine bone marrow stromal cells (M2-10B4) were grown to confluency in RPMI medium plus 10 fetal calf serum in T-150 flasks (Falcon) and irradiated at 2,000 RAD to prevent the bone marrow cells from overgrowing. All cells in the medium were removed and the M2-10B4 cells were overlaid with 35 ml fresh complete media (IMDM+ 12.5% FCS+12.5% horse serum+$10^{-6}$M hydrocortisone)(LTBMC medium) and cultured for 4 days. Half of the media was then replaced by fresh complete media and $Na_2^{35}SO_4$ (Carrier free, Specific Activity 43 Ci/mg, ICN Biomedicals, Irvine, Calif.) for 24 hours to label the glycoproteins. The supernatant was then pooled and frozen at $-70°$ C.

2. Size Fractionation of Stroma Conditioned Media

To examine the nature of the soluble factors in the conditioned media, the media was size fractionated by ultrafiltration. The media was ultrafiltered in a first step through a 100 kD (YM100) membrane (concentrate=fraction>100 kD). The eluate was then passed through a 50 kD (XM50) membrane (concentrate=fraction>50 kD<100 kD) and the ultrafiltrate then passed through a 1 kD (YM1) membrane (concentrate=fraction<50 kD).

Figure 2:
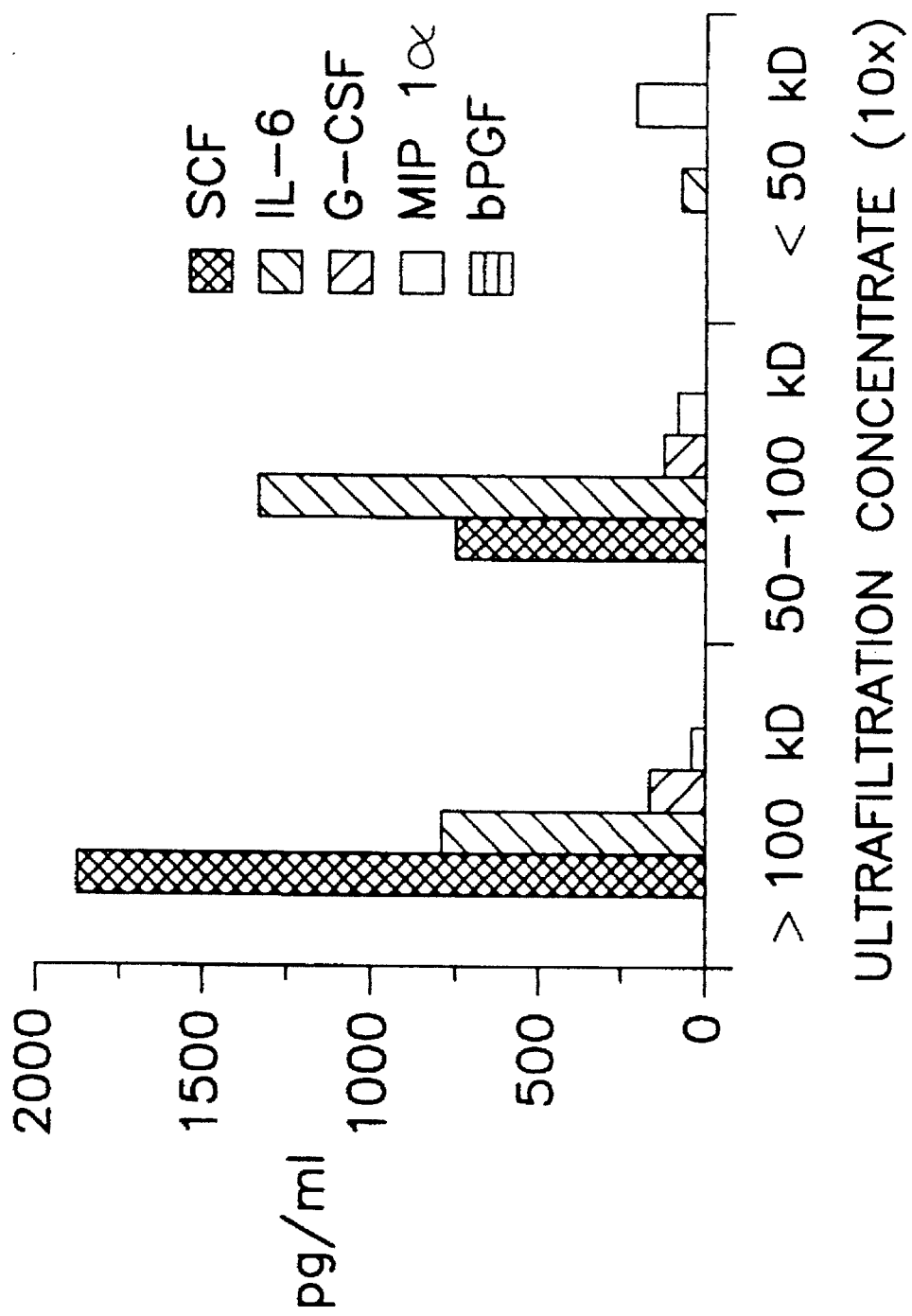
FIG. 2 is a graphical depiction of the concentration of various cytokines in three different molecular weight fractions obtained from stroma conditioned media.

FIG. 2 is a graphic depiction of the size fractionated protein content in the conditioned versus nonconditioned media. The fractions were then analyzed for the presence or absence of cytokines and as shown in FIG. 2, it was demonstrated that cytokines were present in all three fractions. Electrophoresis further demonstrated that molecules of >60 kD were not present in the <50 kD fraction and that molecules of >120 kD were absent from the >50 kD fraction.

Figure 3:
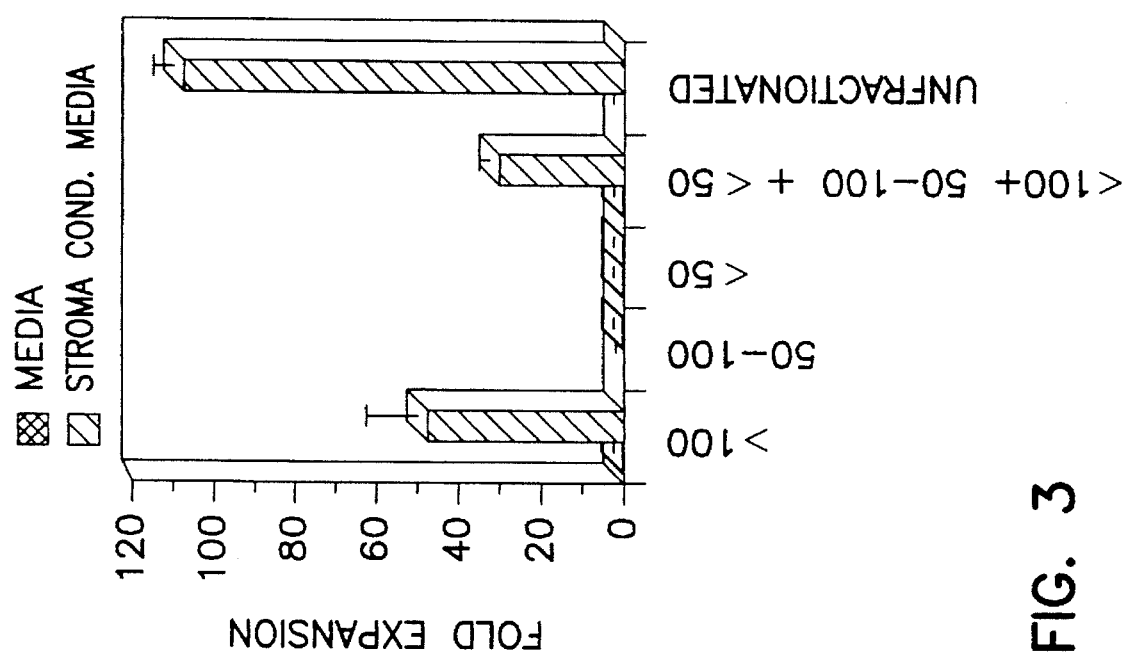
FIG. 3 is a graphical depiction of the expansion of Lin$^-$/CD34$^+$/HLA-DR$^-$ cells in cultures augmented with different molecular weight fractions obtained from stroma conditioned media and control media.
Figure 4:
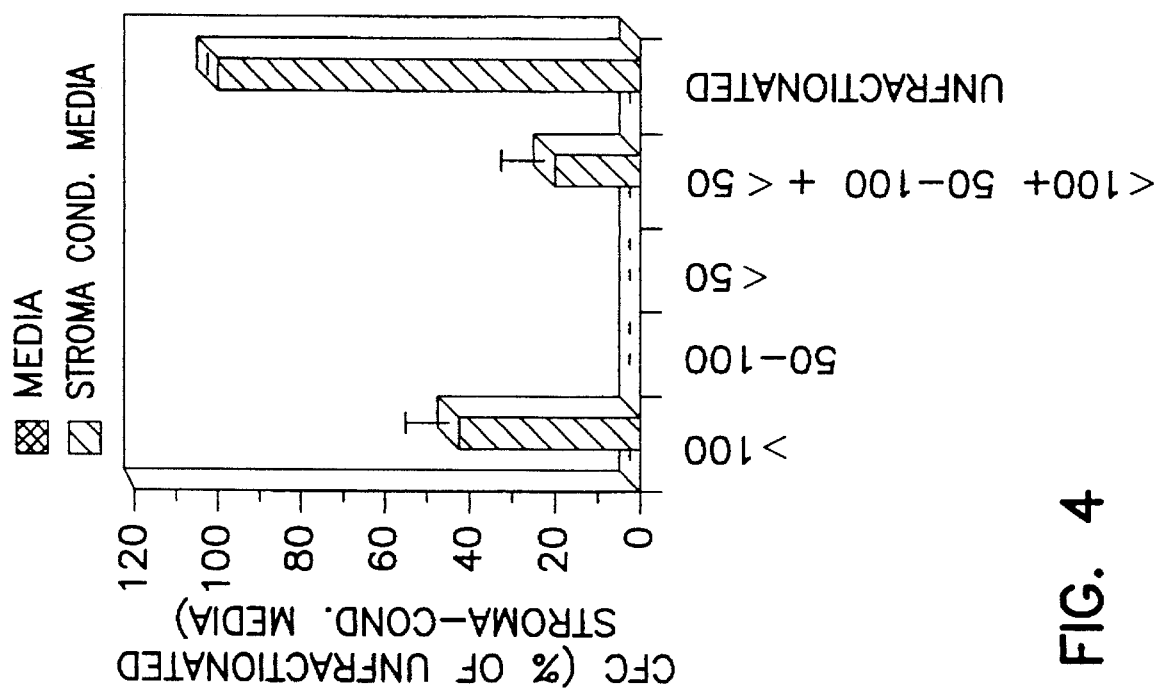
FIG. 4 is a graphical depiction of the generation of colony forming units (CFC) in cultures treated with different molecular weight fractions obtained from stroma conditioned media.

These fractions were then evaluated for their ability to support growth of purified $Lin^-/CD34^+/HLA-DR^-$ cells. These cells were plated in Transwell inserts of empty wells and fed 6/7 days with the different fractions for a total of 5 weeks. Cells present in the Transwells were them evaluated for the number of committed CFC by methylcellulose progenitor assay or in secondary LTBMC (in limiting dilution analysis) to determine the conservation of more primitive LTBMC-IC. As is shown in FIGS. 3 and 4, the active factor(s) are present exclusively in the large molecular weight fraction of the supernatants and excluded from the low molecular weight fractions which do, however, contain similar amounts of cytokines as the larger molecular weight fractions.

3. Purification of Proteoglycans and Glycoproteins

Portions of the supernatant from the M2-10B4 conditioned media were thawed and prior to chromatography, dialyzed into starting buffer for the DEAE columns (DEAE buffer: 0.05M TRIS base, 6.0 mM urea, 0.1M NaCl, 0.01M EDTA, 0.01M 6-aminohexanoic acid, 0.2% 3-[(3-Cholamidopropyl)-dimethylammonio]- 1-propane-sulfonate (CHAPS), 0.1 mM Phenylmethylsulfonyl Fluoride (PMSF), pH 7.0). Sulphated glycoproteins were then concentrated by high performance liquid chromatography (HPLC) with a 7.5×7.5 mm TSK DEAE 5PW anion exchange column (BioRad, Richmond, Va.) using a linear salt gradient from 0.1M to 0.8M aqueous NaCl. Peaks removed between 0.15 and 0.6M NaCl were pooled. The salt gradient was monitored using a Radiometer Conductivity Meter (Model CDM 83). To insure adequate separation of $^{35}S$-proteoglycans (PG), HPLC-DEAE chromatographic peaks were each rechromatographed on the same column prior to further characterization. Recovery of radioactivity from the DEAE-HPLC columns was routinely 80%. This fraction was employed in the culture systems described in Example 3.

Figure 5:
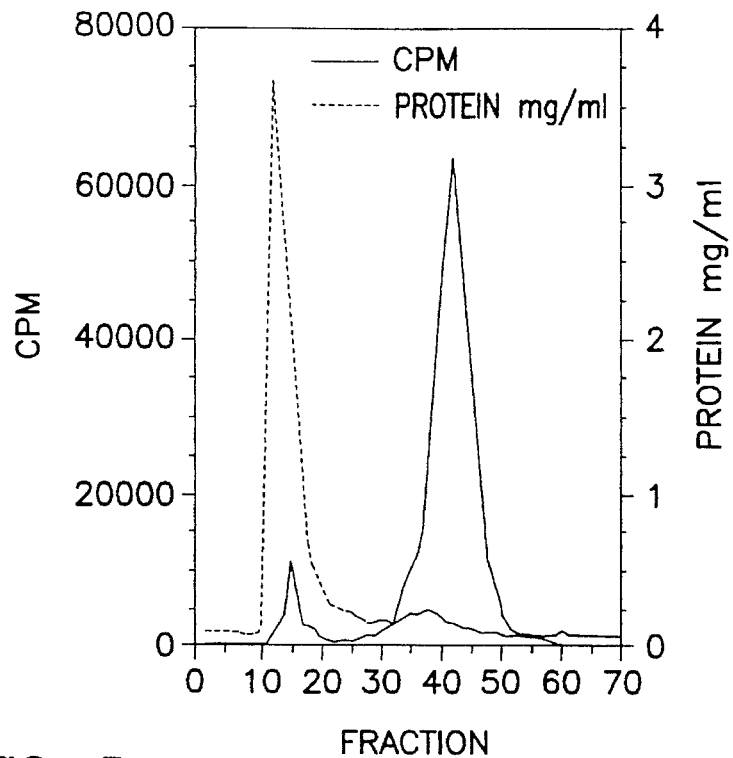
FIG. 5 is a chromatogram of the radiolabelled HPLC eluant from stromal conditioned media, wherein the dashed line indicates the protein fraction, including glycoproteins, and the solid line represents the radiolabelled proteoglycan fraction.

The GAG types within the supernatant were evaluated by gel filtration of the supernatant on Sepharose G-50 (Sigma) columns. The columns were equilibrated and eluted with a mixture of 8.72 ml formic acid, 16.9 ml $NH_4OH$, pH 6.0 and 0.02% sodium azide in 2 liters at a flow rate of 3 ml/hr. The resulting chromatogram is shown in FIG. 5. $^{35}$S-GAG's were released from the proteoglycan core proteins by alkaline borohydride reduction, neutralized and desalted on Sephadex G-50 (Sigma) columns. $^{35}$S-GAG's were recovered from the $V_o$ with less than 5% of alkali released material included in the column.

The main GAG's present in M2-B104 supernatant were found to be heparan sulphate and a smaller fraction of chondroitin sulphate. The heparan sulphate or chondroitin sulphate content of the $^{35}$S-GAG samples was determined by nitrous acid deaminative cleavage and chondroitinase ABC (Seikagaku Smerica Inc.) treatment and was found to be 90% and 10%, respectively. The molecular weight of the proteogylcans was found to be >200 kD, the core protein of the chondroitin sulphate proteoglycan was found to have a molecular weight of approximately 90 kD while that for the heparin sulphate proteoglycan had a molecular weight of 65 kD, as measured by SDS-PAGE, under reducing or non-reducing conditions.

EXAMPLE 3

Culture of "Stroma-Free" Stem Cells

The HPLC fractions obtained from the stroma conditioned media in Example 2 (as shown in FIG. 5) were then evaluated for their ability to support conservation and differentiation of human LTBMC-IC in media with two different concentration mixtures of cytokines. The $^{35}$S radiolabel was allowed to decay for 70 days before use of the eluates.

In the first group, Lin$^-$/CD34$^+$/HLA-DR$^-$ cells were cultured for 5 weeks in stroma conditioned media, unconditioned media, media containing concentrations of cytokines usually found in stroma conditioned media (500 pg/ml G-CSF, 50 pg/ml GM-CSF, 200 pg/ml SCF, 50 pg/ml LIF, 2 ng/ml IL-6, 200 pg/ml MIP-1α), the HPLC eluate of Example 2, or the HPLC eluate plus the cytokines. As shown in Table 2, the combined use of the HPLC eluate and the cytokines supported conservation and differentiation of LTBMC-IC to the same extent as stroma-conditioned media, while either component alone failed to do so.

TABLE 2

|  | LTC-IC* | CFC/5000 DR- |
|---|---|---|
| BM stroma conditioned media | 100 ± 0 | 512 ± 44 |
| LTBMC media alone | 3 ± 3 | 0 ± 0 |
| Cytokine combination | 2 ± 2 | 0 ± 0 |
| HPLC elute | 3 ± 3 | 0 ± 0 |
| HPLC elute + cytokines | 92 ± 20 | 840 ± 120 |

*As % of BM stroma conditioned media; determined by replating DR- progeny in LDA on stroma for 5 weeks.

Figure 6:
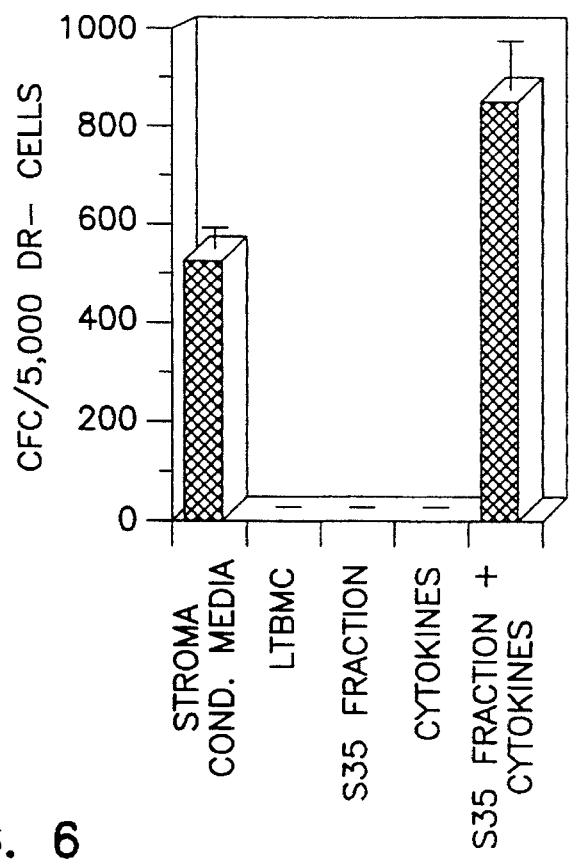
FIG. 6 is a graphical depiction of the generation of colony forming units in cultures treated with the radiolabelled ($S^{35}$) molecular weight fractions isolated from stroma conditioned media with and without added cytokines.
Figure 7:
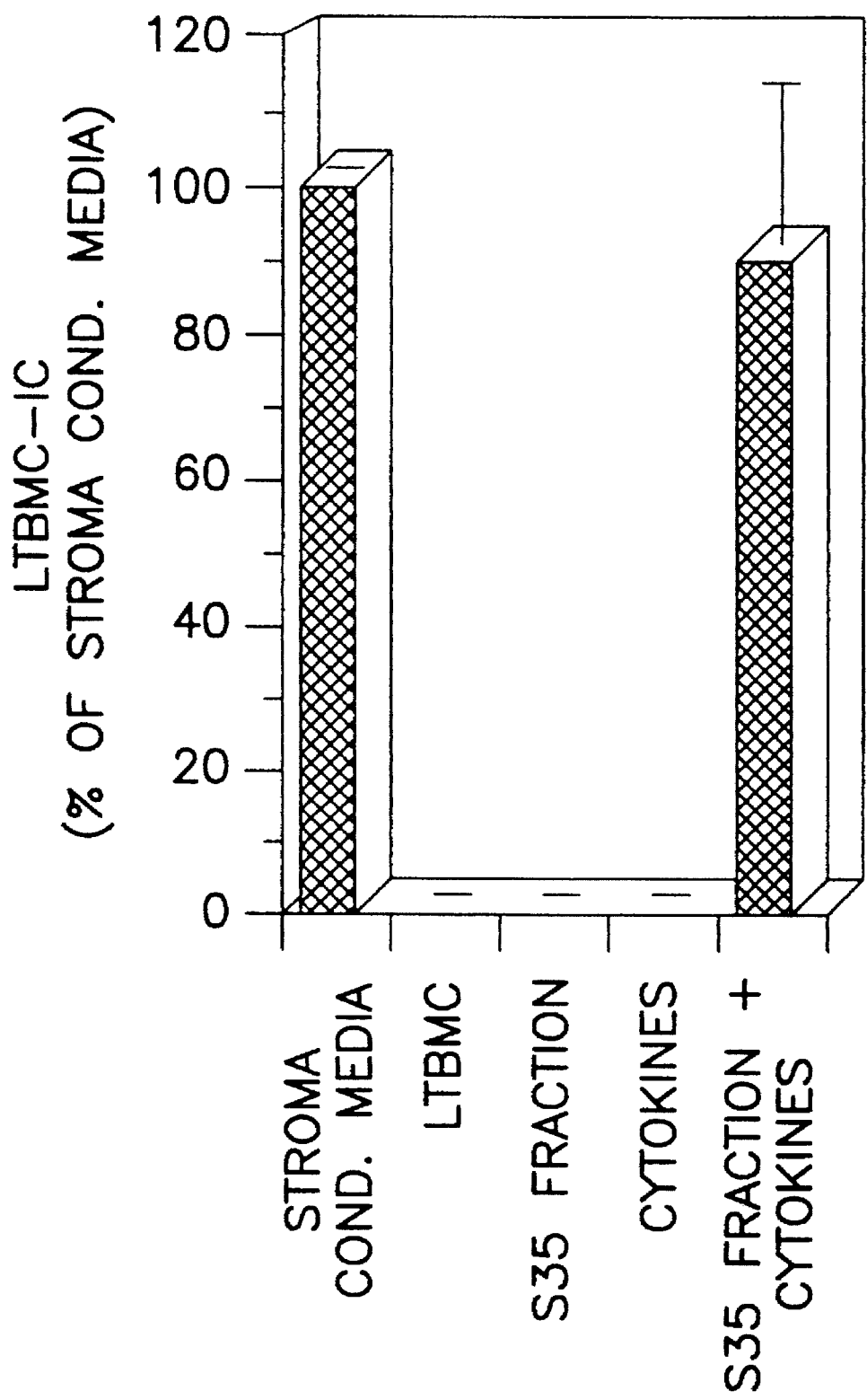
FIG. 7 is a graphical depiction of the 5-week maintenance of LTBMC-IC by the molecular weight fractions obtained from stroma conditioned media with added cytokines.

In a second experiment, the fraction of Example 2 was resuspended in compete media containing cytokines in amounts usually detected in stromal supernatants (500 pg/ml IL-6, 200 pg/ml G-CSF, 100 pg/ml SCF, 100 pg/ml MIP-1α, 50 pg/ml LIF, 50 pg/ml GM-CSF), and then evaluated for its ability to support the growth of Lin$^-$/CD34$^+$/HLA-DR$^-$ cells. These cells were plated in Transwell inserts of and placed in stroma-free wells with complete media and treated for 6/7 days with the mixtures indicated in FIGS. 6 and 7 for a total of 5 weeks. Cells present in the Transwells were then evaluated for the number of committed CFC by methylcellulose progenitor assay or in secondary LTBMC (in limiting dilution assay) to determine the conservation of more primitive LTBMC-IC. As shown in FIGS. 6 and 7, LTBMC media alone, LTBMC media with added cytokines but without glycoproteins/GAG's ("cytokines") and LTBMC media with glycoproteins/GAG's only ("$^{35}$S fraction") did not maintain LTBMC-IC or promote differentiation, while both M2-10B4 conditioned media without cytokines and a combination of the $^{35}$S glycoprotein/GAG fraction and cytokines maintained both LTBMC-IC and CFC proliferation.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition, capable of promoting differentiation and maintaining the self-renewal capacity of long-term bone marrow culture-initiating cells in a mammalian hematopoietic cell culture, said composition prepared by a process comprising:

subjecting an aqueous culture medium conditioned by stromal cells to ion exchange chromatography to obtain a fraction comprising two anionic proteoglycans;

wherein one of said two proteoglycans has a molecular weight of greater than 200 kD as measured by SDS-PAGE under reducing conditions, and comprises a core protein and a polysaccharide portion which comprises chondroitin sulfate; and wherein the other of said two proteoglycans has a molecular weight of greater than 200 kD as measured by SDS-PAGE under reducing conditions, and comprises a core protein and a polysaccharide portion which comprises heparan sulfate.

2. The composition of claim 1 wherein said core protein, of the proteoglycan which comprises chondroitin sulfate, has a molecular weight of about 90 kD.

3. The composition of claim 1 wherein said core protein, of the proteoglycan which comprises heparan sulfate, has a molecular weight of about 65 kD.

4. A proteoglycan having a molecular weight of greater than about 200 kD, comprising:

a core protein having a molecular weight of about 65 kD, and a polysaccharide portion which comprises heparan sulfate;

wherein said proteoglycan is capable of promoting differentiation and maintaining the self-renewal capacity of long-term bone marrow culture-initiating cells in a mammalian hematopoietic cell culture.

\* \* \* \* \*